(12) United States Patent
Ongaro et al.

(10) Patent No.: US 9,737,626 B2
(45) Date of Patent: Aug. 22, 2017

(54) AUTOCLAVE FOR MEDICAL-DENTAL USE

(75) Inventors: Daniele Ongaro, Villa di Serio (IT);
Mariapia Ghilardi, Villa di Serio (IT)

(73) Assignee: NAKANISHI INC., Tochigi (JP)

( * ) Notice: Subject to any disclaimer, the term of this patent is extended or adjusted under 35 U.S.C. 154(b) by 603 days.

(21) Appl. No.: 14/233,101

(22) PCT Filed: May 28, 2012

(86) PCT No.: PCT/IB2012/052657
§ 371 (c)(1),
(2), (4) Date: Jan. 15, 2014

(87) PCT Pub. No.: WO2013/011388
PCT Pub. Date: Jan. 24, 2013

(65) Prior Publication Data
US 2014/0161666 A1 Jun. 12, 2014

(30) Foreign Application Priority Data
Jul. 15, 2011 (IT) .............................. MI2011A1318

(51) Int. Cl.
*A61L 2/07* (2006.01)
*A61L 2/26* (2006.01)

(52) U.S. Cl.
CPC ...... *A61L 2/26* (2013.01); *A61L 2/07* (2013.01); *A61L 2202/13* (2013.01)

(58) Field of Classification Search
CPC ..... A61L 2/07; A61L 2/24; A61L 2/26; A61L 2202/122; A61L 2202/13
See application file for complete search history.

(56) References Cited

U.S. PATENT DOCUMENTS

| 5,173,258 A | 12/1992 | Childers |
| 6,319,463 B1 | 11/2001 | Celli |

FOREIGN PATENT DOCUMENTS

| EP | 0654274 A1 | 5/1995 |
| EP | 1481692 A1 | 12/2004 |

*Primary Examiner* — Timothy Cleveland
(74) *Attorney, Agent, or Firm* — Vorys, Sater, Seymour & Pease LLP

(57) ABSTRACT

Provided is an autoclave for medical-dental instruments and the like, including a sterilization chamber, an accumulator, a main channel connecting the sterilization chamber and the accumulator in circuit and bringing them into communication for fluid passage, a pump adapted to move the fluid inside the main channel, in which the accumulator includes a volume of a material having hygroscopic properties resulting from an exothermic reaction and vice versa.

5 Claims, 5 Drawing Sheets

AUTOCLAVE FOR MEDICAL-DENTAL USE

The present invention relates to a steam disinfector or steriliser hereinafter referred to as autoclave, in particular for medical-dental use, of the type pointed out in the preamble of the first claim.

Presently known are autoclaves for sterilisation of medical instruments. They act by means of saturated steam at high temperatures and pressures which is sent to the inside of a chamber in which the instruments to be sterilised are placed.

The autoclaves themselves therefore comprise a sterilisation chamber within which the instruments to be sterilised are inserted and humidification and heating apparatus adapted to create saturated steam at high temperatures and pressures. The air is then purged through ejection of steam mixed with air or through fractional vacuum.

They further comprise means for obtaining a hot air flow adapted to carry out drying of the instruments inside the sterilisation chamber when sterilisation has been completed, and evacuation from the sterilisation chamber. In addition, drying can take place by vacuum (utilising the heat latent present in the instruments), by vacuum and heat radiation, by ventilation. The most efficient combination is radiation under vacuum followed by ventilation of dry and filtered hot air.

Autoclaves are increasingly more used because they allow full and accurate sterilisation without use of dangerous chemical substances.

In fact, instruments sterilised by use of chemical substances must be deeply rinsed to prevent said chemical substances from remaining on the medical instruments subsequently used for surgical operations or the like.

On the contrary, it is not necessary to rinse steam coming from filtered water because the same is not at all dangerous.

In particular, for dental use small autoclaves are employed which are of simple and convenient use, that can be located in laboratories of small sizes.

The above mentioned known art however has some important drawbacks.

In fact, a high amount of thermal energy is required for operation of autoclaves.

In particular, each autoclave must carry out sterilisation phases with steam at high temperature and also drying phases through air at high temperature or also under vacuum or using both phases simultaneously or alternately.

In addition, it is necessary to provide evacuation systems for the used-up steam and hot water. These evacuation systems cannot coincide with the external environment because this environment often consists of the dental laboratory itself. It is therefore necessary to conceive complicated evacuation and cooling systems.

Another drawback resides in that the correct drying time of the instruments disposed in the autoclave cannot be always foreseen in a simple manner. In fact it is not possible to look at the inside of the sterilisation chamber that is submitted to high temperatures and pressures and it is therefore necessary to calculate a long time for being sure that drying of the instruments has taken place in a proper manner. This inexactitude in calculating the drying time further increases the amount of energy used by the autoclave.

Under this situation, the technical task underlying the present invention is to provide an autoclave in particular for medical-dental use capable of substantially obviating the mentioned drawbacks.

Within the scope of this technical task, it is an important aim of the invention to obtain an autoclave in particular for dental use, involving a reduced energy consumption.

The technical task mentioned and the aims specified are achieved by an autoclave in particular for dental use, as claimed in the appended claim 1.

Preferred embodiments are highlighted in the sub-claims.

The features and advantages of the invention are hereinafter clarified by the detailed description of a preferred embodiment of the invention, with reference to the accompanying drawings, in which.

Figure 1:
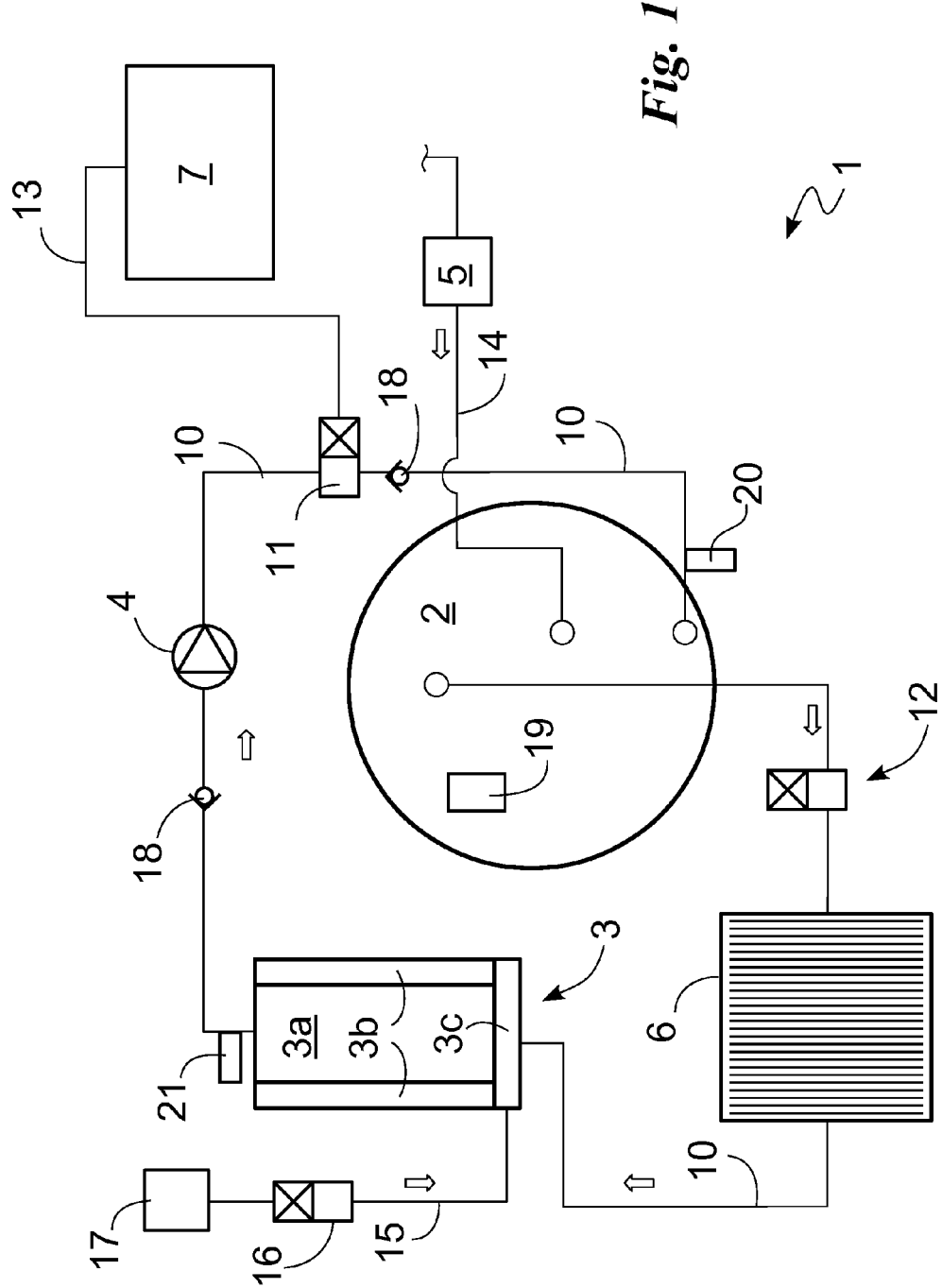
FIG. 1 shows a first diagrammatic view of the autoclave according to the invention.

With reference to the aforesaid figures, the autoclave according to the invention is generally denoted at 1.

It substantially consists of a sterilisation system for medical-dental instruments and the like, using steam at high pressures and temperatures.

It briefly comprises: a sterilisation chamber 2, an accumulator 3 as hereinafter better characterised, at least one pump 4, and preferably also: a steam generator 5, a heat exchanger 6 and at least one discharge tank 7.

In greater detail the sterilisation chamber 2 is a sterilisation chamber of reduced volume for dental instruments and the like. It is known by itself, is made of steel and has a substantially cylindrical shape.

Accumulator 3 advantageously comprises a volume 3a of a material having hygroscopic properties resulting from an exothermic reaction and vice versa, and a heater 3b for volume 3a, preferably of the electric type. Substantially when volume 3a absorbs steam or moisture, it emits dry hot air and, on the contrary, when it absorbs heat, from heater 3b for example, it emits steam. Therefore it substantially allows storage of energy and recirculation of same so that said energy must not be evacuated in the environment, as better pointed out hereinafter. A material having said hygroscopic properties resulting from an exothermic reaction and vice versa is zeolite, for example.

Accumulator 3 finally comprises a container 3c for the condensate, at the lower part thereof.

Pump 4 is adapted to carry out fluid transfers between the different elements, as hereinafter specified, and is advantageously a piston pump, or alternatively a diaphragm pump. As an alternative, pump 4 may consist of a fan or any other means suitable for fluid transfer.

The steam generator 5 is known by itself and consists of a resistor or the like in contact with the demineralised-water tank, so that it is able to generate heat to be introduced into the sterilisation chamber 2.

The heat exchanger 6 is substantially a radiator for fluids, known by itself, that is air- or liquid-cooled, and the discharge tank 7 is adapted to store the used-up fluids. It preferably consists of a first tank for liquids 7a and a second tank for aeriform substances 7b.

Said elements are connected to each other by means of channels and ducts forming the same and valves adapted to cut off or not said channels.

In particular, a main channel 10 connects in circuit and brings into communication for fluid passage: the sterilisation chamber 2, heat exchanger 6, accumulator 4, pump 4 and sterilisation chamber 2 again, preferably following the stated order.

Preferably some on-off valves are present along the main channel. In particular a first valve 11 is disposed between pump 4 and the sterilisation chamber 2, a second valve set 12 is on the contrary disposed between the sterilisation chamber 2 and the heat exchanger 6.

Figure 2:
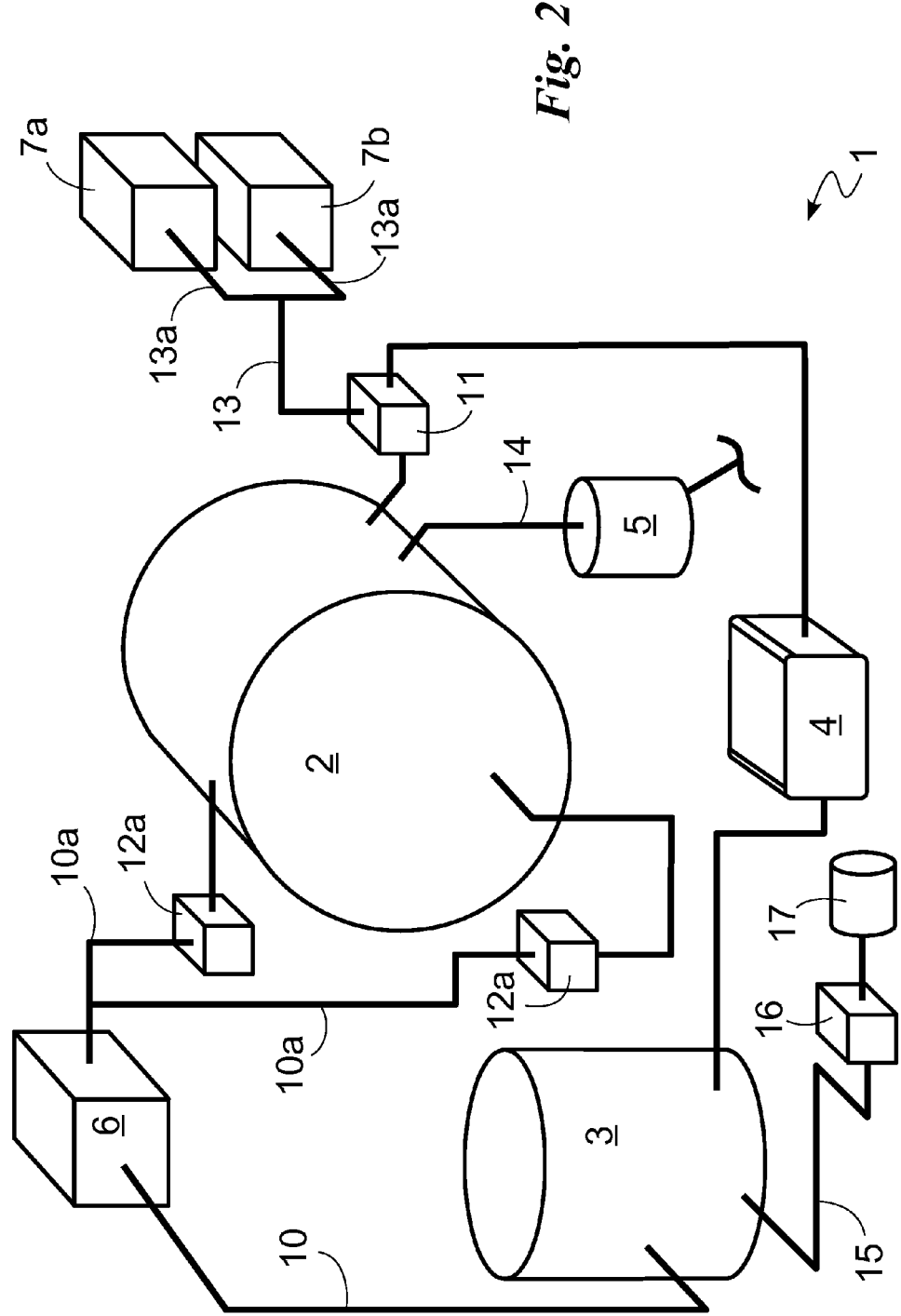
FIG. 2 is a second diagrammatic view of the autoclave of the invention.

In addition, the main channel 10, as shown in FIG. 2, comprises a forked portion joining the sterilisation chamber 2 and the heat exchanger 6. This forked portion therefore comprises two separated ducts 10a, one intended for evacuation of the condensate mixed with steam from the sterilisation chamber 2 and disposed at the lower part thereof, and one intended for drawing and disposed at the upper part of the sterilisation chamber 2. These ducts 10a are cut off by the valve set 12 that therefore consists of two separated valves 12a, one on each duct 10a.

A discharge channel 13 is then provided and it connects the main channel 10, in particular the stretch from pump 4 to the sterilisation chamber 2, to the discharge tank 7. Connection between the discharge channel 13 and the main channel 10 is suitably provided at the first valve 11 that advantageously in this case consists of a three-way valve, adapted to alternately connect either pump 4 to the discharge tank 7 closing connection to the sterilisation chamber 2 or pump 4 to the sterilisation chamber 2 closing connection to the discharge tank 7. Alternatively, two different two-way valves can be provided.

The exhaust channel 13 too is preferably forked into two portions 13a connected to the tanks for liquids 7a and for aeriform substances 7b.

Further provided is a loading channel 14 adapted to connect the steam generator 5 with the sterilisation chamber and possibly provided with valves and diaphragm pumps, or vibration pumps or the like, and a connecting channel 15 adapted to connect the accumulator 3 to the external environment or the tank for aeriform substances. The connecting channel 15 is suitably provided with a second valve 16 and a bacteriological purification filter 17 adapted to filter the air entering accumulator 3.

The channels, and in particular the main channel 10, can finally comprise nonreturn valves 18 to ensure correct circulation of the fluid and prevent return of same.

Conveniently, the autoclave 1 finally comprises sensors such as a main sensor 19 adapted to measure temperature and pressure inside the sterilisation chamber 2 and also, advantageously, a thermoregulation sensor, merely referred to as inlet thermometer 20, adapted to measure the flow temperature at the entry of the main channel 10 into the sterilisation chamber 2. Also present may be another thermoregulation sensor, merely referred to as second thermometer 21, at the accumulator 3 or the accumulator exit.

Operation of the autoclave 1, structurally described above, is the following. This operation defines a new sterilisation process 50 for different instruments and in particular dental instruments.

At the beginning, the sterilisation chamber 2 is at room temperature and the atmosphere consists of air that is not disinfected or sterilised, while volume 3a is filled with the internally collected moisture coming from a previous sterilisation cycle.

The sterilisation chamber 2 can therefore be opened and is manually accessible and the dental instruments or the like can be loaded.

Figure 3A:
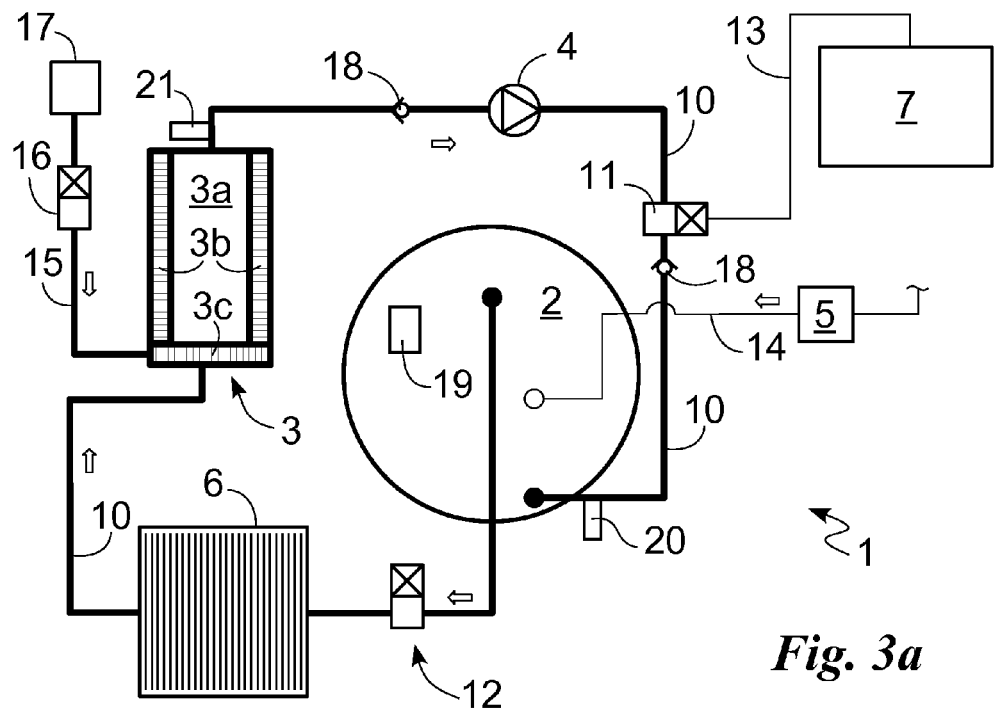
FIGS. 3a-3d show the diagram of FIG. 2 in several different operating phases.

A regeneration phase 51 begins (FIG. 3a) during which regeneration of volume 3a, of zeolite or other material, present in the accumulator 3 takes place.

By the term "regeneration" it is intended the process by which through heater 3b, volume 3a is heated in such a manner that it emits steam until its full dehydration. The reverse process, i.e. the hydration process with emission of dry hot air, is referred to as absorption.

During the regeneration phase 51 in a first part heater 3b heats volume 3a that will emit steam. The steam is carried from pump 4 along the main channel 10, through the first valve 11 and therefrom to the sterilisation chamber 2 that will start pre-heating. During this process the second valve 16 is now and then opened to supply volume 3a with sterile air, as this volume, due to filter 17 otherwise would become under vacuum.

Subsequently, in a second part of the regeneration phase 51, carried out together with the first part or alternatively at different alternated moments, the first and second valves 11 and 16 are closed and the valve set 12 is open. Steam is transferred from the sterilisation chamber 2 to the heat exchanger 6 where it condenses and settles in container 3c at the base of the accumulator 3 in the form of condensate.

The extraction phase 52 begins, this phase aiming at fully emptying the sterilisation chamber 2 from the air and exclusively filling it with steam that better sterilises the instruments.

Figure 3B:
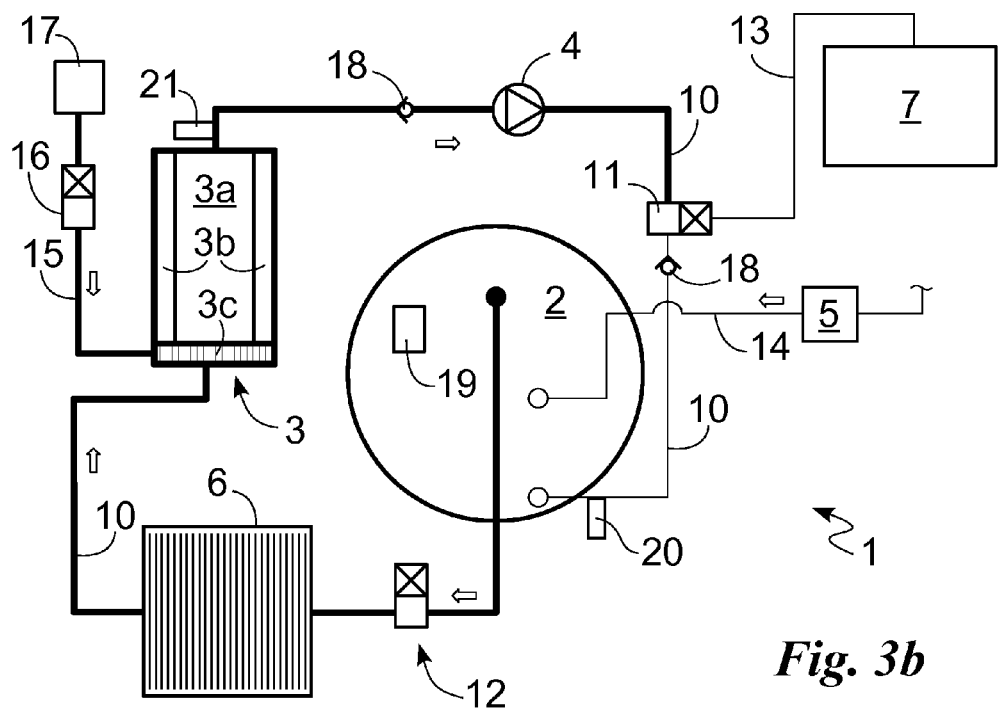

The extraction phase 52 is suitably of the type described in the Italian patent IT-B-1265206 between the first line, page 5, and the second-last paragraph of page 16 and in FIG. 2b. In fact, in a first discharge sub-phase 52a (FIG. 3b) of the extraction phase 52 the sterilisation chamber 2 is brought under vacuum, until about a pressure included between −0.8 and −0-9 bars of relative pressure.

In particular, during this first sub-phase 52a the valve set 12 is in the open position and the first valve 11 connects the main channel 10 to the discharge tank 7, closing the inlet portion to the sterilisation chamber 2.

Air and steam present in the sterilisation chamber 2 are therefore transferred, still through pump 4, to the heat exchanger 6 and therefrom to the accumulator 3 that will retain the transferred steam. The remaining dry air is then transferred to pump 4 and the discharge tank 7.

Then the second loading sub-phase 52b starts (FIG. 3c) in which steam is introduced into the sterilisation chamber 2 so as to bring it to a relative pressure included between 0.3 and 1.2 bars.

During this phase the sterilisation chamber 2 is closed; the valve set 12 and in some cases the first valve 11 too close the main duct, while the steam generator 5 supplies the sterilisation chamber 2 until said pressure is reached. In addition, preferably other steam can be supplied by accumulator 3 and in particular by volume 3a of zeolite. This steam is then transferred to the sterilisation chamber 2.

In a third discharge sub-phase 52c (FIG. 3b), the steam is at least partly exhausted from the sterilisation chamber 2 so as to bring it to a relative pressure included between −0.9 and 0.4 bars. In this sub-phase 52c, steam and air are conveyed to volume 3a and internally stored.

Figure 4A:
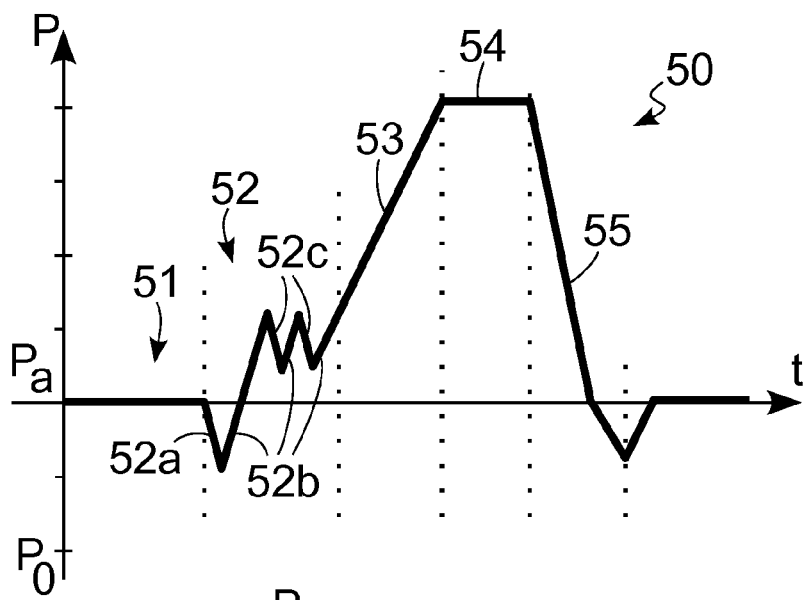
FIGS. 4a-4c are time-pressure grafts of the sterilisation process according to the invention.
Figure 4B:
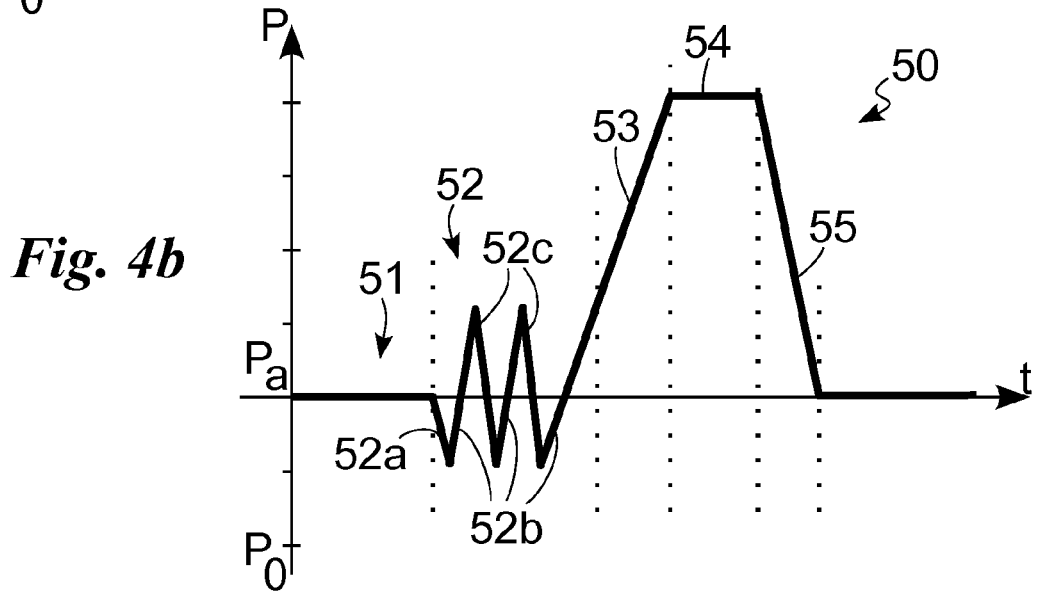
Figure 4C:
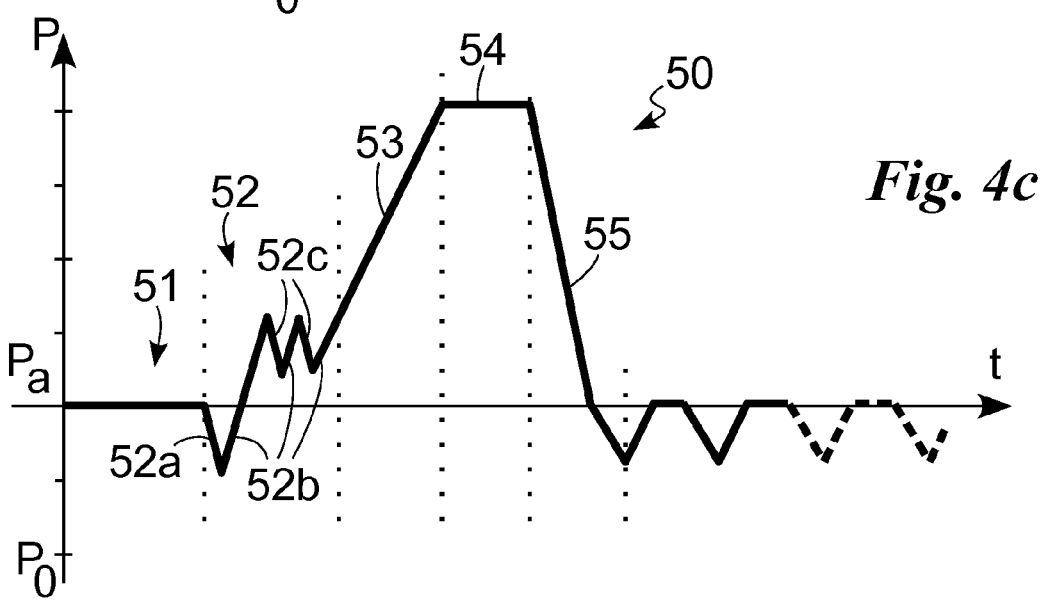

As shown in FIG. 4a and in FIG. 4c, in this phase the relative pressure in the sterilisation chamber 2 can be positive or negative as shown in FIG. 4b. In particular, during this third sub-phase 52c settings are identical with settings of the first sub-phase 52a, with the only difference that the steam percentage in the channels is much greater and accumulator 3, and more particularly the zeolite volume 3a, is greatly charged with the steam itself.

Said second sub-phase 52b and third sub-phase 52c can be repeated several times so as to almost fully eliminate the air present in the sterilisation chamber 2 and optimise sterilisation through steam. This expedient is in particular described in the mentioned patent IT-B-1265206.

It is also possible to check whether the inner environment of the sterilisation chamber 2 is fully made up of steam by verifying that the inner pressure and temperature, measured by sensor 19, are in proportions very close to the theoretical proportions of the steam-state diagrams.

Figure 3C:
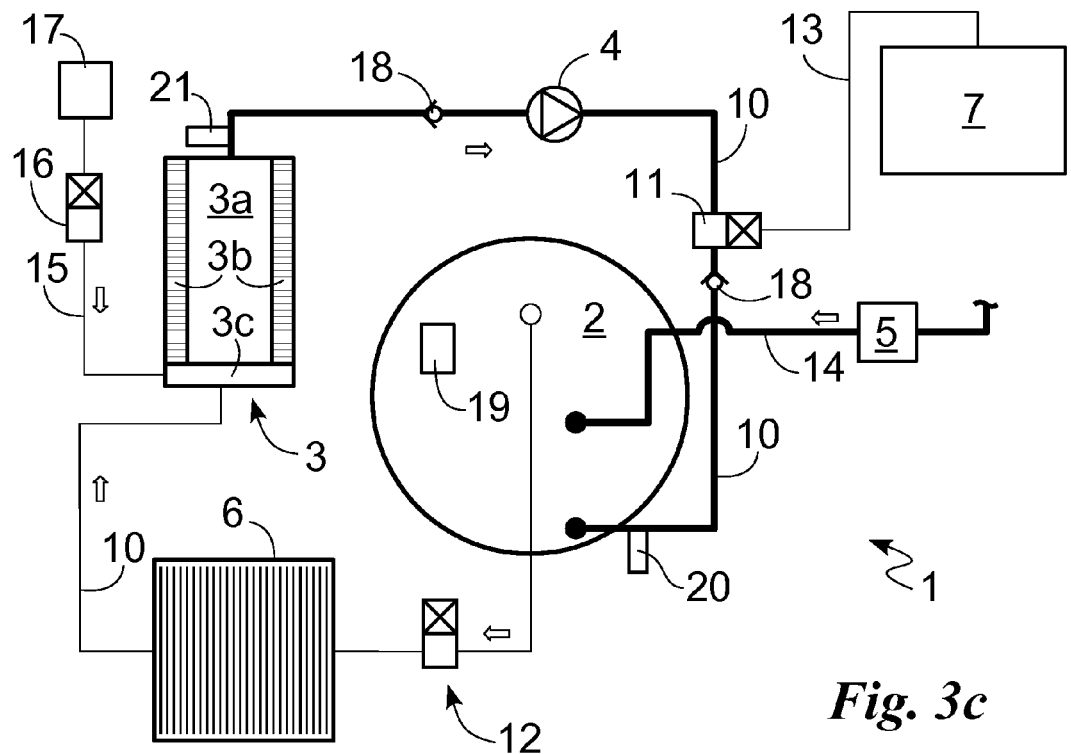

After a predetermined number of cycles or when sensor 19 measures the correct percentage of steam inside the sterilisation chamber 2, the loading phase 53 begins (FIG. 3c).

At the beginning of this phase accumulator 3, and more particularly the zeolite volume 3a, is charged with steam. This steam is then transferred to the sterilisation chamber 2.

Heater 3b heats then volume 3a regenerating it. The latter emits steam through the main channel 10.

The steam passes through the pump 4, the first valve 11 that connects accumulator 3 to the sterilisation chamber 2 closing the way to the discharge tank 7, the steam enters the sterilisation chamber 2 and pressurises it, until a relative pressure included between 1.8 and 2.2 bars, since the valve set 12 is in the closed position.

In addition, during this loading phase 53 preferably the steam generator 5 too supplies the sterilisation chamber 2, until said pressure.

When the loading phase 53 has been completed, the sterilisation phase 54 begins; during this phase the sterilisation chamber is isolated as the valve set 12 and the first valve 11 close the main duct, and the loading channel 14 too is closed. Therefore sterilisation of the instruments inside the sterilisation chamber 2 is carried out by the steam.

At the end of sterilisation, accumulator 3, and in particular volume 3a is dry, since it has emitted all the steam.

Figure 3D:
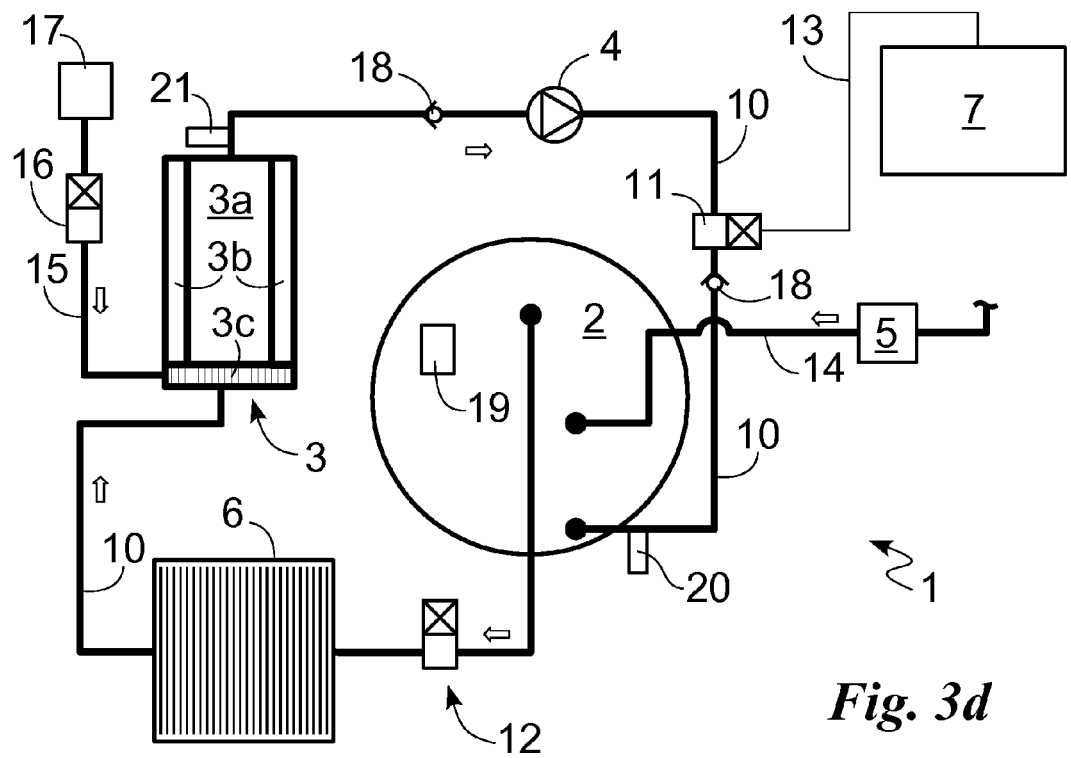

Then the drying phase 55 begins (FIG. 3d). During this phase the hot air flow generated in volume 3a by absorption in said material is utilised.

In particular, the valve set 12 and the first valve 11 are in the open position, the way to the discharge tank 7 is closed and the main channel 10 is fully open.

In this case the steam is sent to the heat exchanger 6 and then to accumulator 3. The latter absorbs the steam and emits dry hot air. The dry hot air reaches pump 4 that is always carrying out fluid transfers, passes through the first valve 11 and goes back to the sterilisation chamber 2. The cycle continues and the air coming out of the sterilisation chamber 2 is increasingly drier and the air coming out of accumulator 3 increasingly less hot, by effect of the absorption phase of volume 3a, as previously described. Drying can alternatively contemplate alternated phase of vacuum and room pressure (FIG. 4c) or exclusively phases of room pressure.

The instruments then dry and the thermometer 20 measures the temperature at the entry of the sterilisation chamber 2. This drying can arrive at a vacuum of the sterilisation chamber 2.

When the drying phase 55 has been completed, possibly cooling of the instruments is waited for, and then the starting conditions exist again in which the accumulator 3 is charged with steam and the sterilisation chamber 2 is at room temperature and is accessible for extraction of the instruments and introduction of new instruments for a new sterilisation cycle.

The invention achieves important advantages.

In fact, due to the presence of accumulator 3, steam and heat are not lost in the environment but they can be recycled and hot air and steam can be alternately emitted, so that great energy and steam savings can be obtained.

A further advantage is given by the fact that pump 4 is not passed through by the condensate that is in fact retained by accumulator 3. Said pump 4 can therefore consist of a piston pump having higher performances than diaphragm pumps. On the contrary, in the known art, due to the presence of condensate, use of diaphragm pumps was compulsory.

Another advantage also resides in that the thermometer 20 or the second thermometer 21 can measure the drying state of the instruments in the sterilisation chamber 2 in real time. In fact, when the temperature of sensors 20 and 21 goes under a given value, 50° C. for example, and therefore non-hot air is introduced at the entry, this means that steam is no longer present in the sterilisation chamber 2 and that therefore the instruments are now dry.

It is therefore possible to adjust drying based on the instruments present in the sterilisation chamber 2.

A further advantage is represented by the fact that part of the water used can be recycled and therefore it is not necessary to eliminate it from the environment.

The invention is susceptible of variations falling within the scope of the inventive idea expressed by the independent claims and the related technical equivalents.

The invention claimed is:

1. An autoclave for medical-dental instruments, comprising: a sterilization chamber, an accumulator, and a main channel, connecting said sterilization chamber and accumulator in circuit and bringing them into communication for fluid passage, a pump adapted to move said fluid inside said main channel, said fluid being a steam at a high pressure and temperature and said accumulator comprising a volume of a material having hygroscopic properties resulting in an exothermic reaction and configured for emitting dry hot air when it absorbs the steam or moisture and configured for emitting said steam when it absorbs heat.

2. The autoclave as claimed in claim 1, wherein said volume consists of zeolite.

3. The autoclave as claimed in claim 1, wherein said accumulator comprises a heater for said volume.

4. The autoclave as claimed in claim 1, wherein said pump is a piston pump.

5. The autoclave as claimed in claim 1, comprising a thermometer and wherein said main channel comprises two separated ducts, one of said separated ducts being intended for evacuation of a condensate mixed with steam from the sterilization chamber and disposed at a lower part thereof, the other of said separated ducts being intended for drawing and disposed at a upper part of the sterilization chamber, and the thermometer being disposed the first of said separated ducts.

* * * * *